(12) United States Patent
Bierhoff et al.

(10) Patent No.: US 11,576,717 B2
(45) Date of Patent: Feb. 14, 2023

(54) OPTICAL TISSUE FEEDBACK DEVICE FOR AN ELECTROSURGICAL DEVICE

(71) Applicant: KONINKLIJKE PHILIPS N.V., Eindhoven (NL)

(72) Inventors: Waltherus Cornelis Jozef Bierhoff, Veldhoven (NL); Bernardus Hendrikus Wilhelmus Hendriks, Eindhoven (NL); Franciscus Marinus Antonius Maria Van Gaal, Heeze (NL); Torre Michelle Bydlon, Melrose, MA (US); Vishnu Vardhan Pully, Eindhoven (NL); Christian Reich, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 367 days.

(21) Appl. No.: 15/570,102

(22) PCT Filed: Apr. 26, 2016

(86) PCT No.: PCT/EP2016/059237
§ 371 (c)(1),
(2) Date: Oct. 27, 2017

(87) PCT Pub. No.: WO2016/177600
PCT Pub. Date: Nov. 10, 2016

(65) Prior Publication Data
US 2018/0303539 A1    Oct. 25, 2018

(30) Foreign Application Priority Data
May 6, 2015   (EP) .................................... 15166502

(51) Int. Cl.
*A61B 18/14*    (2006.01)
*A61B 5/00*    (2006.01)
(Continued)

(52) U.S. Cl.
CPC .......... *A61B 18/148* (2013.01); *A61B 5/0075* (2013.01); *A61B 5/0084* (2013.01);
(Continued)

(58) Field of Classification Search
CPC ... A61B 18/148; A61B 5/0075; A61B 5/0084; A61B 5/6847; A61B 2017/00057;
(Continued)

(56) References Cited

U.S. PATENT DOCUMENTS

| 4,314,559 A * | 2/1982 | Allen ..................... A61B 18/14 |
| | | 30/140 |
| 4,361,926 A | 12/1982 | Brush et al. |

(Continued)

FOREIGN PATENT DOCUMENTS

| JP | H06205789 A | 7/1994 |
| WO | 2013108194 A2 | 7/2013 |
| WO | 2014207640 A1 | 12/2014 |

OTHER PUBLICATIONS

Nachabe, Rami et al "Estimation of Lipid and Water Concentrations in Scattering Media with Diffuse Optical Spectroscopy from 900 to 1600nm", Journal of Biomedical Optics, vol. 15, No. 3, 2010.
(Continued)

*Primary Examiner* — Jaymi E Della (57) ABSTRACT

A tissue sensing device for use with an electrosurgical knife is proposed which comprises a proximal end portion, a distal end portion and a grip portion there between. The proximal end portion is configured for attachment to a housing of the electrosurgical knife. The distal end portion is configured for movably supporting a blade of the knife. A distal end of an optical fiber is arranged at the distal end portion of the device and a proximal end of the optical fiber is connectable to an optical console, so that optical measurements can be performed at the distal end portion.

25 Claims, 7 Drawing Sheets

(51) Int. Cl.
*A61B 17/00* (2006.01)
*A61B 18/00* (2006.01)

(52) U.S. Cl.
CPC .. *A61B 5/6847* (2013.01); *A61B 2017/00057* (2013.01); *A61B 2017/00061* (2013.01); *A61B 2017/00199* (2013.01); *A61B 2018/0013* (2013.01); *A61B 2018/0097* (2013.01); *A61B 2018/00172* (2013.01); *A61B 2018/00589* (2013.01); *A61B 2018/00601* (2013.01); *A61B 2018/00607* (2013.01); *A61B 2018/00904* (2013.01); *A61B 2018/00976* (2013.01); *A61B 2018/1412* (2013.01); *A61B 2562/0238* (2013.01); *A61B 2562/228* (2013.01)

(58) Field of Classification Search
CPC ........... A61B 2017/00061; A61B 2017/00199; A61B 2018/0013; A61B 2018/00172; A61B 2018/00589; A61B 2018/00601; A61B 2018/00607; A61B 2018/00904; A61B 2018/0097; A61B 2018/00976; A61B 2018/1412; A61B 2562/0238; A61B 2562/223; A61B 2562/228; A61B 2505/05
See application file for complete search history.

(56) References Cited

U.S. PATENT DOCUMENTS

| | | | | |
|---|---|---|---|---|
| 5,376,094 A * | 12/1994 | Kline | ............... | A61B 17/221 606/110 |
| 5,456,681 A * | 10/1995 | Hajjar | ............... | A61B 18/24 15/104.92 |
| 5,498,258 A * | 3/1996 | Hakky | ............. | A61B 17/32002 604/22 |
| 5,857,961 A | 1/1999 | Vanden | | |
| 6,106,524 A * | 8/2000 | Eggers | ............... | A61B 5/0531 606/41 |
| 6,405,733 B1 * | 6/2002 | Fogarty | ............... | A61B 90/39 128/899 |
| 6,770,070 B1 * | 8/2004 | Balbierz | ............... | A61B 10/04 600/566 |
| 2002/0026127 A1 * | 2/2002 | Balbierz | ............. | A61B 18/1477 600/567 |
| 2006/0030753 A1 | 2/2006 | Boutillette | | |
| 2006/0069386 A1 * | 3/2006 | Dubnack | ............ | A61B 18/1402 606/41 |
| 2006/0173359 A1 * | 8/2006 | Lin | ............... | A61B 5/4244 600/478 |
| 2006/0184161 A1 * | 8/2006 | Maahs | ............... | A61B 18/1492 606/2 |
| 2007/0112343 A1 * | 5/2007 | Mische | ................. | A61B 18/02 606/41 |
| 2007/0239033 A1 * | 10/2007 | Tearney | ............... | A61B 5/0059 600/476 |
| 2009/0275840 A1 * | 11/2009 | Roschak | ............. | A61B 5/0084 600/467 |
| 2013/0023910 A1 * | 1/2013 | Solomon | ............. | A61B 5/4887 606/158 |
| 2015/0005765 A1 | 1/2015 | Hendriks | | |

OTHER PUBLICATIONS

Parrel, T.J. et al "A Diffusion Theory Model of Spatially Resolved, Steady-State Diffuse Reflectance for the Non-Invasive Determination of Tissue Optical Properties", Medical Physics, vol. 19, No. 4, 1992, pp. 879-888.
Nachabe, Rami et al "Estimation of Biological Chromophores using Diffuse Optical Spectroscopy: Benefit of Extending the UV-VIS Wavelength Range to Include 1000 to 1600 nm" Optics Express, vol. 18, No. 24, 2010, pp. 1432-1442.
Zhang, Qingguo. et al "Turbidity-Free Fluorescence Spectroscopy of Biological Tissue", Optics Letters, vol. 25, No. 19, 2000, pp. 1451-1453.
Nachabe, Rami et al "Effect of Bile Absorption Coefficients on the Estimation of Liver Tissue Optical Properties anti Related Implications in Discriminating Healthy and Tumorous Samples", Biomedical Optics Express, vol. 2, No. 3, 2011.

* cited by examiner

OPTICAL TISSUE FEEDBACK DEVICE FOR AN ELECTROSURGICAL DEVICE

CROSS-REFERENCE TO PRIOR APPLICATIONS

This application is the U.S. National Phase application under 35 U.S.C. §371 of International Application No. PCT/EP2016/059237, filed on Apr. 26, 2016, which claims the benefit of European Patent Application No. 15166502.3, filed on May 6, 2015. These applications are hereby incorporated by reference herein.

FIELD OF THE INVENTION

The invention generally relates to a device for tissue sensing and a system for electro-surgery including the same. Particularly, the invention relates to a device having optical fibers for tissue sensing, wherein the device is configured to be attached to an electrosurgical knife.

BACKGROUND OF THE INVENTION

In electrosurgery a high-frequency electric current is applied to tissue in order to cut, coagulate, desiccate, or fulgurate tissue. The fact that it is used in 80% or more of all surgical procedures already indicates the usefulness of the device. Depending on the tissue in front of the device the surgeon can decide on which operating mode of the device is used.

During breast tumor surgery, for instance a lumpectomy, the surgeon aims to remove the breast tumor without leaving behind more than a focally positive margin i.e. the surgeon wants to avoid leaving behind substantial portions of the tumor because this would lead to recurrence of the tumor. Small microscopic portions that are left behind can be treated by additional radiotherapy treatment.

Although the surgeon can make a mental picture of the tumor from pre-operative images, such as images taken during mammography, during surgery there is no feedback regarding the tumor. Due to this lack of feedback during surgery a significant amount of surgeries result in positive margins and additional surgical procedures are required.

Various ways have been proposed to provide feedback during the surgical procedure, for instance, by performing a pathology test during the procedure such as frozen section analysis or touch-preparation cytology. Another option is by inspecting the resected specimens with optical spectroscopy. These options are all cumbersome because when a positive margin is detected on the resected specimen it is difficult to find the exact location in the body where additional tissue must be resected due to positivity.

In a patent application WO 2013/108194 an electrosurgical knife was proposed with optical tissue sensing incorporated. What is not addressed in this application is for example the problem that during the cutting procedure with the electrosurgical knife debris may stick to the blade that may obscure the optical tissue sensing.

In document US20070239033, an apparatus is described for identifying characteristics of a blood vessel contained within a tissue. In this, a radiation source provides radiation to the tissue and a probe receives radiation returned from the tissue. Data relating to the tissue is processed and used to indicate whether the blood vessel is in a vicinity of an end portion of the probe.

There are many other surgical procedures where discriminating tissues is also important, the breast case is only given as an example. The importance of discriminating tissues is not limited to oncology procedures but could also be necessary in orthopedic, neuro, or cardiovascular procedures to name a few.

SUMMARY OF THE INVENTION

The general problem is to improve the optical sensing facility in electro-surgery so as to get more reliable measurements of tissue. This is achieved by the subject-matter of the independent claim. Further embodiments are described in the dependent claims.

A further problem may be to provide a medical device with an electrosurgical tool having optical tissue feedback which may be mounted on a blade of an electrosurgical knife and which is configured to change its position such that it is at the proximal portion of the blade during cutting and at the distal side when optically sensing the tissue.

To solve the problems, an optical tissue sensing device may change the position of at least a part of the device relative to the knife by pressing a lever such that a sensing part is at the proximal portion of the blade during cutting and distally when optically sensing the tissue. The device may comprise a lever close to an activation button of the electrosurgical knife such that the movement of the device can be activated near that position. In the proximal position, no or at least less debris may reach the optical sensing element of the device during cutting, i.e. this prevents obscuring the optical measurements.

It will be understood that it is also possible to use the sensing device during the cutting process. In this case the sensing console may be linked to the cutting console so that the cutting process can be controlled by the sensing console. For instance the control can be established by making a connection between the plug of the electrosurgical knife and the socket of the electrical console.

Another way may be to produce a signal from the optical console during the cutting process that indicates that a critical structure is nearby. The signal can be in any form like visible, acoustic, vibration, indication on a screen etc.

In general, a tissue sensing device for use with an electrosurgical knife comprises a body and an optical fiber. The body, which may be in the form of a sleeve, includes a proximal end portion, a distal end portion and a grip portion there between. The proximal end portion, i.e. the portion which when in use is closer to the operator of the device, is configured for attachment to a housing of the electrosurgical knife, for example by receiving a portion of its housing. The distal end portion, i.e. the portion which in use points away from the operator, is configured for movably supporting a blade of the knife. In other words, at least the distal end portion of the body is movable relative to and at the blade of the electrosurgical knife. A distal end of the optical fiber is arranged at the distal end portion of the body and a proximal end of the optical fiber is connectable to an optical console, so that optical measurements can be performed at the distal end portion of the body, preferably at the front surface of the distal end portion of the body. The distal end of the optical fiber is thus positioned separately to the blade; i.e. the distal end of the optical fiber does not form part of the blade. In so doing the cleaning or disposal cycles of these components can be determined independently; i.e. the blade may be re-used whereas the optical fiber may be a single use component.

According to an embodiment the tissue sensing device may further comprise a guiding tube, wherein the optical fiber may be movably accommodated within the guiding tube. The optical fiber may be retracted into the guiding tube to protect the fiber end when the optical fiber is not in use.

According to another embodiment, the tissue sensing device may further comprise a protection plug which may be arranged at the distal end of the optical fiber and which is configured to transmit light from and/or to the optical fiber. The protection plug may have a shape and may be arranged so as to function as a lens for the transmitted light. Furthermore, the protection plug may close any gap at a guiding tube to avoid any debris or tissue or liquids to enter the gap.

Furthermore, the tissue sensing device may comprise a cleaning element configured for cleaning the tip of the optical fiber when the optical fiber is moving inside the guiding tube. For example, the cleaning element may be a kind of a brush arranged in or at a guiding tube or another element so that the optical fiber may be in contact with the brush and may be moved along the brush.

According to an embodiment the optical fiber may be movable relative to the distal end portion of the body so that the distal end of the optical fiber protrudes beyond the distal end portion of the body. By way of this the front surface of the optical fiber may be brought into close contact with tissue in front of the distal end portion of the body.

The tissue sensing device may further comprise a fiber connector at the body for optically connecting the optical fiber with the optical console. In other words, an additional optical cable may be used to connect the optical fiber of the tissue sensing device with the optical console.

According to another embodiment, a system may be provided including the above described device as well as a console including a light source, a light detector and a processing unit for processing the signals provided by the light detector, wherein one of the light source and the light detector may provide wavelength selectivity. The light source may be one of a laser, a light-emitting diode or a filtered light source, and the console may further comprise one of a fiber switch, a beam splitter, a grating, or a dichroic beam combiner. Furthermore, the device may be adapted to perform at least one out of the group consisting of diffuse reflectance spectroscopy, diffuse optical tomography, differential path length spectroscopy, fluorescence spectroscopy, and Raman spectroscopy.

According to another aspect, a system is proposed with an electrosurgical knife and a tissue sensing device as described above. The knife may comprise a housing for attachment to the proximal end portion of the tissue sensing device and a blade configured to be movably supported by the distal end portion of the tissue sensing device.

The tissue sensing device and/or the electrosurgical knife may comprise a lever for moving the distal end portion of the tissue sensing device between a first position in which the distal end portion is located at a tip portion of the blade, and a second position in which the distal end portion is located near the housing of the knife.

According to another embodiment, an elastic element may be provided for biasing the distal end portion of the tissue sensing device in a direction to the tip portion of the blade.

According to yet another embodiment, the grip portion of the tissue sensing device may be configured to be elastically deformed so as to move the distal end portion relative to the blade of the knife.

Not only a cleaning element for cleaning the optical fibers may be provided, but also a means for cleaning the blade of the knife. The means for cleaning the blade may be arranged at the distal end portion of the tissue sensing device so as to be in contact with the blade, thus cleaning the blade by moving the distal end portion of the tissue sensing device along the blade. The blade may alternatively or additionally be coated with an anti-sticking layer.

The system may further comprise an electrical console for providing electrical current to the blade of the knife.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

A tissue sensing device is proposed which is configured to be mechanically attached to an electrosurgical knife, and which is capable of being in at least two positions, a proximal and a distal position. The tissue sensing device further includes at least one optical fiber with the distal end of the fiber at the tip of the device, the fiber being capable of sending and receiving light. The optical fiber may be connected to an optical console capable of sending light and receiving light and able to analyze the received light. With this arrangement, the tissue type in front of the tissue sensing device can be determined and a signal depending on the tissue type can be generated.

Further, a system is proposed which comprises an electrosurgical tool like a knife connected to an electrical console, wherein the tool may be capable to cut, coagulate, desiccate, or fulgurate tissue based on the operation of the electrical console, and a tissue sensing device attached to that tool.

Figure 1:
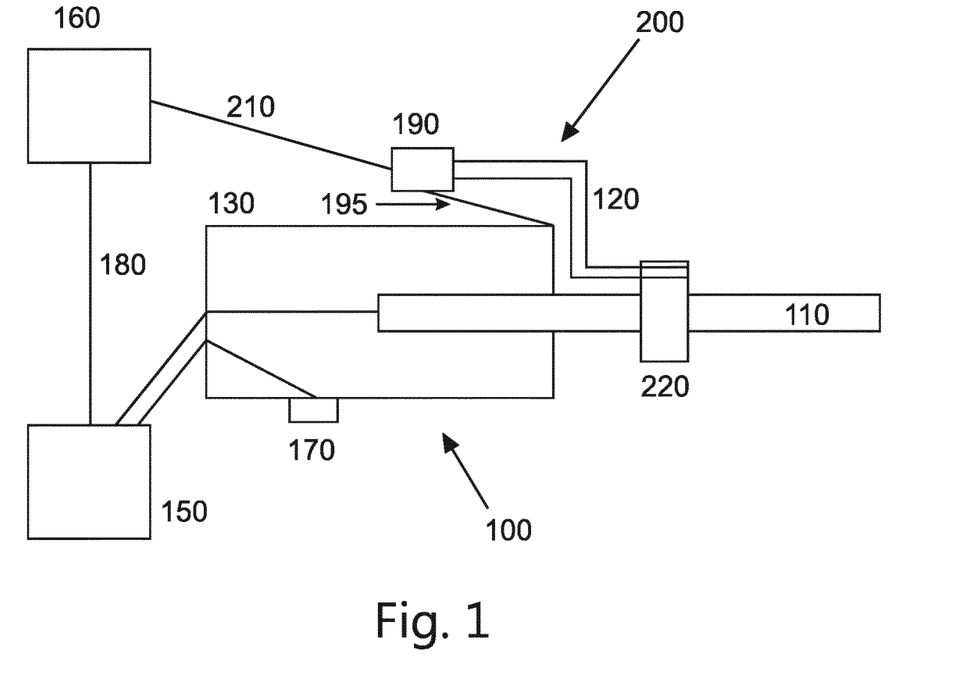
FIG. 1 is a schematic illustration of a system with a tissue sensing device in a first position relative to an electrosurgical knife.
Figure 2:
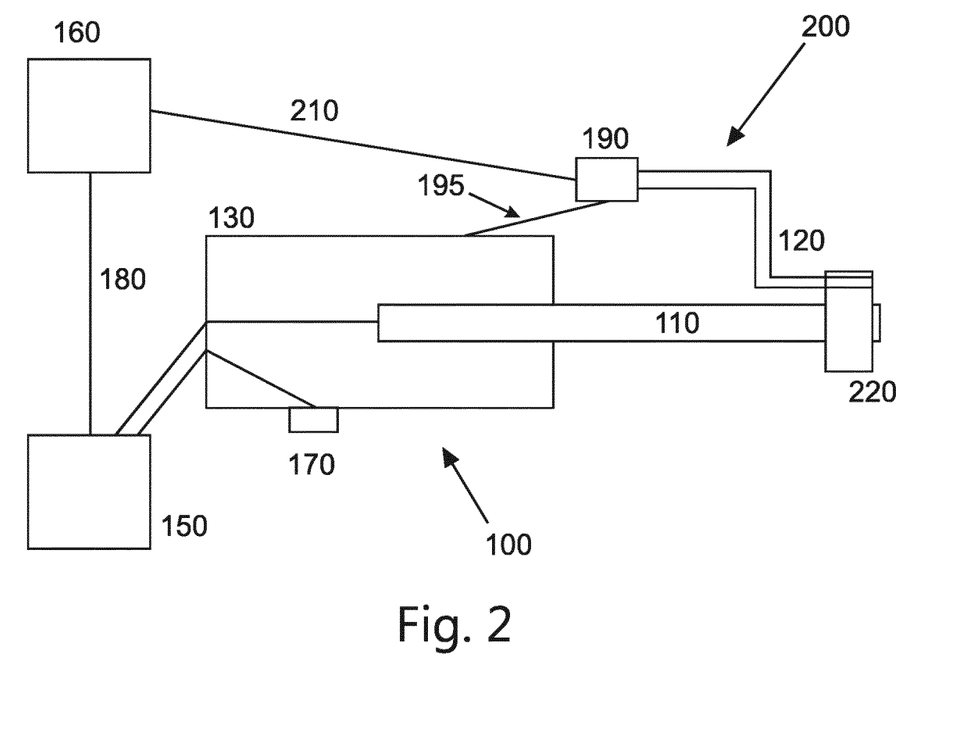
FIG. 2 is a schematic illustration of a system with a tissue sensing device in a second position relative to an electrosurgical knife.

FIGS. 1 and 2 are schematic illustrations of a system including a tissue sensing device 200 and an electrosurgical knife 100 with a blade 110. The device 200 has two optical fibers 120. The optical fibers are connected by means of an optical connector 190 and an optical cable 210 to an optical console 160. The blade 110 is electrically connected to an electrical console 150 capable of sending electrical signal to the blade inducing various treatments such as to cut, coagulate, desiccate, or fulgurate tissue. The blade is capable of performing these treatments to the tissue that is in contact with the blade. One of the optical fibers 120 is connected to a light source in the optical console 160 illuminating the tissue when in contact to the tissue sensing device 200. Scattered light that has travelled through the tissue in contact with the tissue sensing device is collected by a second optical fiber 120 and directed towards the optical console 160. Here the light is spectrally analyzed. From the spectral signatures the tissue type in front of or in direct vicinity of the blade can be determined. For instance using a white light source and detecting the diffusely reflected light it is possible to detect the presence and concentration of various chromophores such as water and fat content. Also fluorescence detection can be used to determine tissue composition.

Figure 3A:
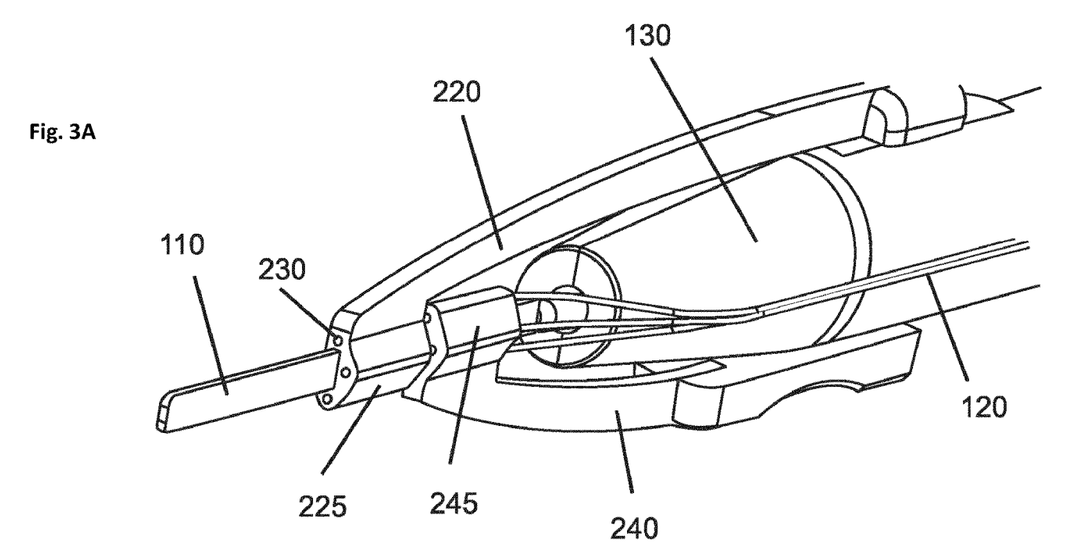
FIGS. 3A and 3B show embodiments of a tissue sensing device with an electrosurgical knife.
Figure 3B:
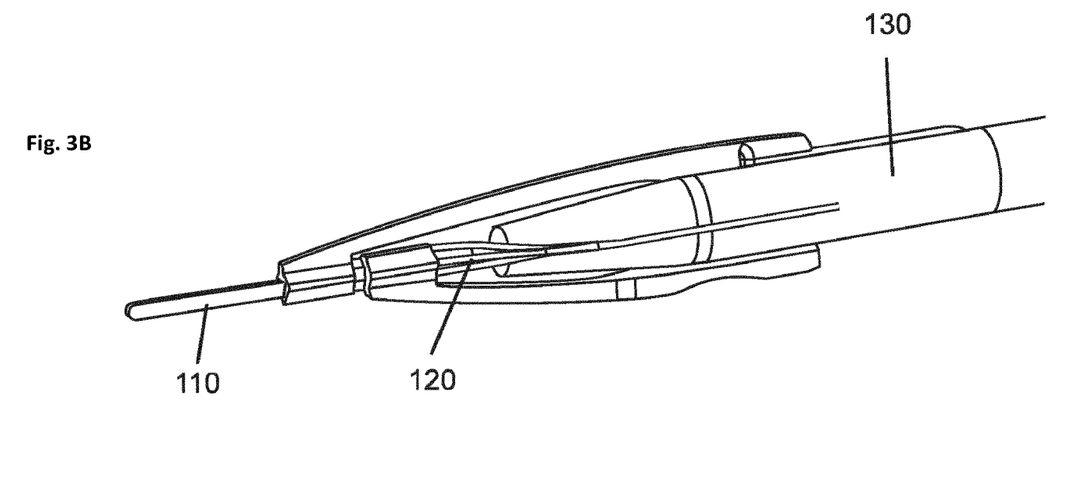
Figure 4:
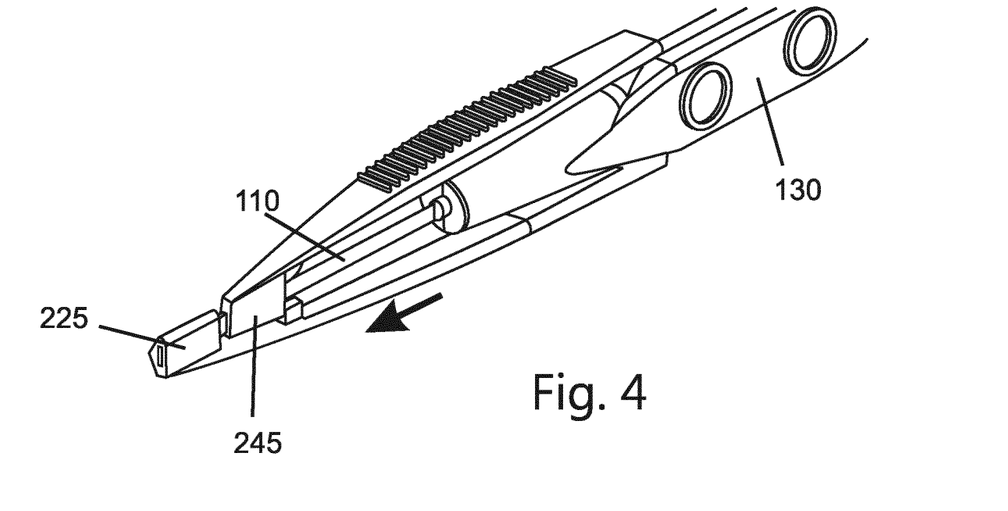
FIG. 4 shows an embodiment of a tissue sensing device with two grip parts being in a first position relative to each other.
Figure 5:
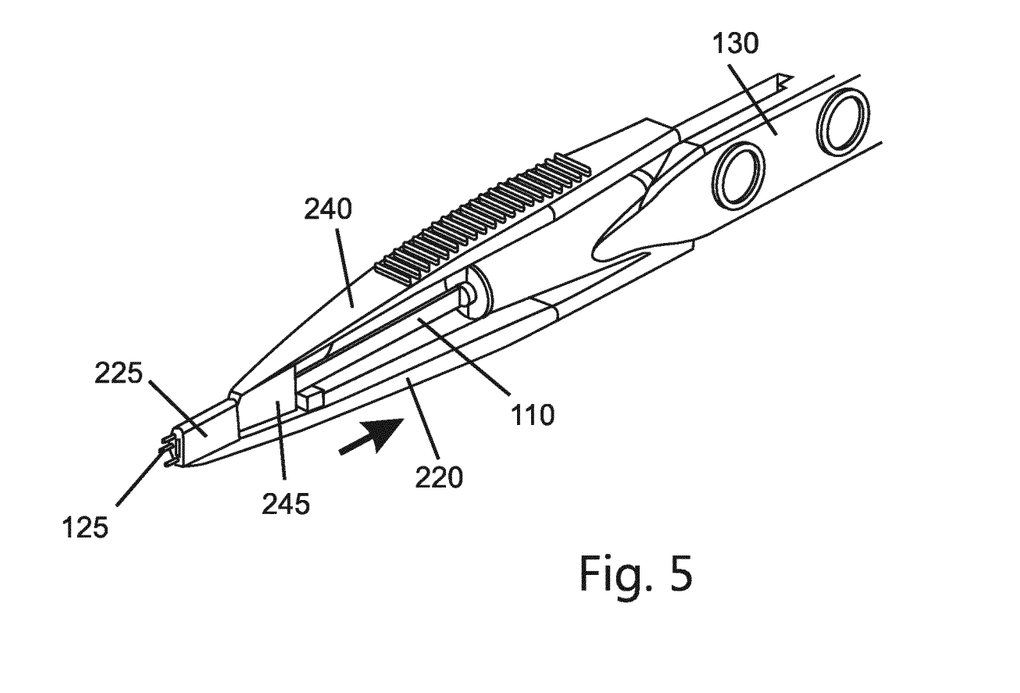
FIG. 5 shows an embodiment of a tissue sensing device with two grip parts being in a second position relative to each other.

Although FIGS. 1 and 2 show an embodiment with two fibers it is also possible to use only one or more than two fibers. In the case of three fibers as shown for example in FIGS. 3A and 3B it is also possible to obtain directional information. For instance using the bottom and the middle fiber as a source-detector pair and compare this with the information of the middle and upper fiber as source-detector pair, the difference in signal provides information about the difference in tissue in both directions.

A trigger or switch 170 may be provided at a housing 130 of the knife 100 to select different operating modes depending on the signal displayed on the optical console 160. Optionally a feedback loop 180 may be present that interferes with the operating mode of the electrical console 150.

Furthermore, the tissue sensing device 200 may have a lever 195 that can be switched from the first mode where the device 200 is in a proximal position at the blade, as illustrated in FIG. 1, to the second mode being in a distal position, as illustrated in FIG. 2. For example, in the first mode the electrosurgery knife may be used for cutting, when in the second mode the device can perform tissue sensing. It is also possible to use the second mode during the cutting. In this way the feedback information from the optical console can directly be used to interrupt the cutting when a critical structure is approached.

In FIGS. 3A to 5 an embodiment is shown in which the tissue sensing device comprises two elements 220, 240 each having a proximal portion for attachment to the housing 120 of an electrosurgical knife, and a distal end portion 225, 245 for accommodating the blade 110 of the knife. The tissue sensing device according to this embodiment can be positioned in three configurations. In the first configuration (see FIG. 3) the tissue sensing device 200 is in the proximal position and the electrosurgical knife with its blade protruding distally from the tissue sensing device, can be used in a standard way. In configuration 2 shown in FIG. 4, the tissue sensing device is advanced to the distal end portion of the blade 110. The tissue sensing device can now be used as a probe to measure the tissue in contact with and/or in front of the blade. In configuration 3 shown in FIG. 5, the tissue sensing device is still at the tip of the blade 110 but the first element 220 is moved relative to the second element 240 such that the fiber ends 125 of the optical fibers 120 are now protruding beyond the distal end portion 225 of the first element 220 of the tissue sensing device. Depending on the position of the tissue sensing device, the optical fiber ends 125 may also protrude beyond the tip of the blade. In this way the fibers may be forced into close contact with the tissue in front of the blade. This allows measuring the tissue that will be cut and allows therefore for corrective action prior to cutting. For instance when a clear margin of several millimeters is required and the probing depth of the source-detector fiber combination in configuration 2 is too shallow, this option allows for depth measurements at any depth. Three fibers could also be used with different separation distances between the fibers. Two fibers could have a short separation distance, while the other combination of two fibers has a larger separation distance. This could allow for shallow and deep probing of the tissue and give a better indication of the critical structure in front of the knife.

In an embodiment, the tissue sensing device may have a cleaning function such that, when advanced forward towards the distal end of the blade, removes debris present on the blade. Various means can be envisioned like a plough used in farming. Furthermore, the blade and/or the tissue sensing device can be coated with an anti-sticking layer. The tissue sensing device may further be combined with a suction device.

Figure 6:
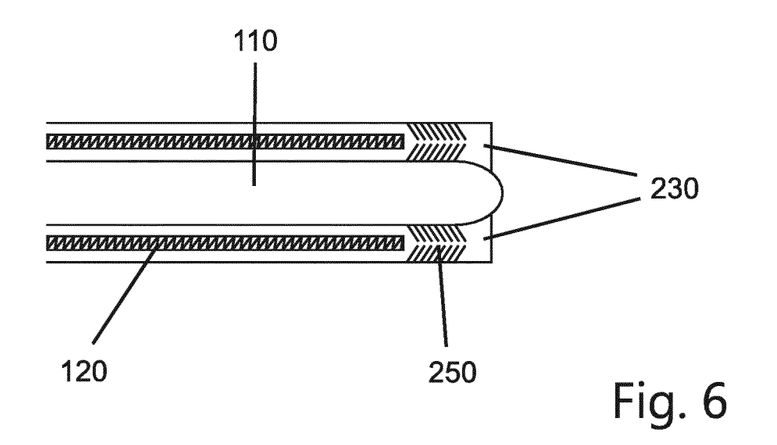
FIG. 6 illustrates an embodiment with means for cleaning the end portion of an optical fiber.

In another embodiment, the optical fibers can be positioned inside an optical port with exits next to the tip of the knife, as shown in FIG. 6. It will be understood that such an optical port may be integrated in for example the distal end portion 225 of the tissue sensing device. Small cleaning brushes 250 can be mounted inside the optical port such that when the optical fibers 120 are extended to the exit 230 of the port the fibers are brushed off (or cleaned) before coming into contact with the tissue. Each time the fibers are retracted and extended to the tip of the knife, they are cleaned off, thus preventing debris from sticking and interfering with the optical signal. Alternatively, the brushes do not even have to be present. The optical fibers could be stored inside the port and extended to the exit when needed.

Figure 7:
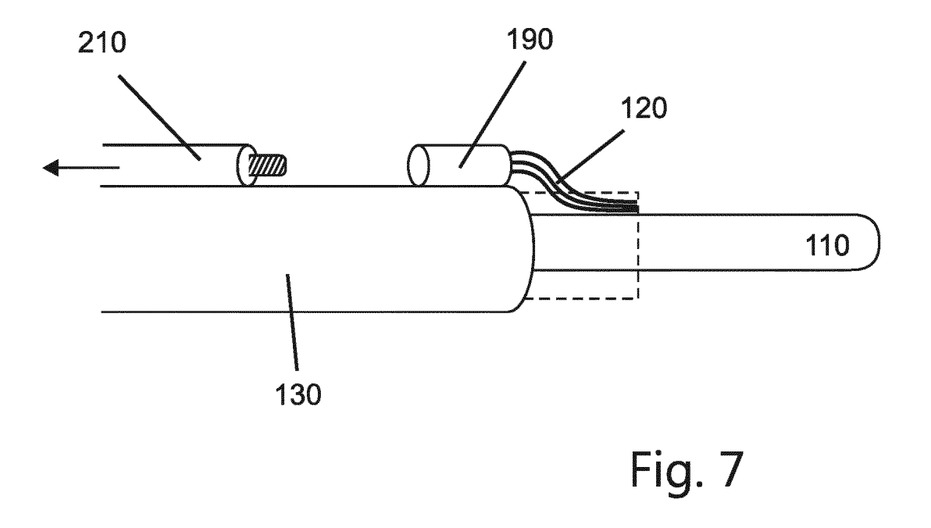
FIG. 7 illustrates an embodiment with an optical fiber connector.

Furthermore, a tissue sensing device may be secured to the end of an electrosurgical knife prior to the procedure starting. The optical fibers could end at an optical connector 190 which may be a female connector as shown in FIG. 7. An optical cable 210 may then be plugged into the receiver when the optical sensing is needed. This gives the surgeon more freedom with the device and he/she does not have an extra cable to deal with in the surgical field.

Figure 8:
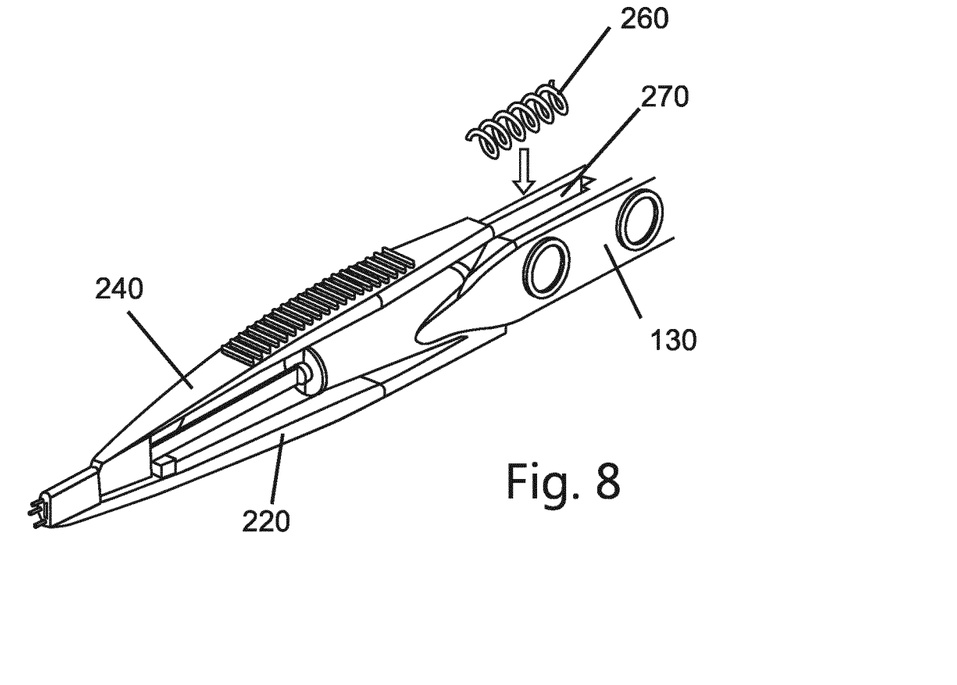
FIG. 8 shows an embodiment with an element for biasing the tissue sensing device in a direction to the distal end of the blade.

As shown in the embodiment of FIG. 8, a biasing element like a spring 260 may be arranged, for example, in a recess 270 and between element 220 and/or 240 of the tissue sensing device and the housing 130 of the knife, to bias the respective element in one of the distal or proximal position. For example, this may help to automatically bring back the mechanical part to the proximal position after it is brought to the distal end of the blade. Also this arrangement could help with cleaning of the blade more easily.

Figure 9:
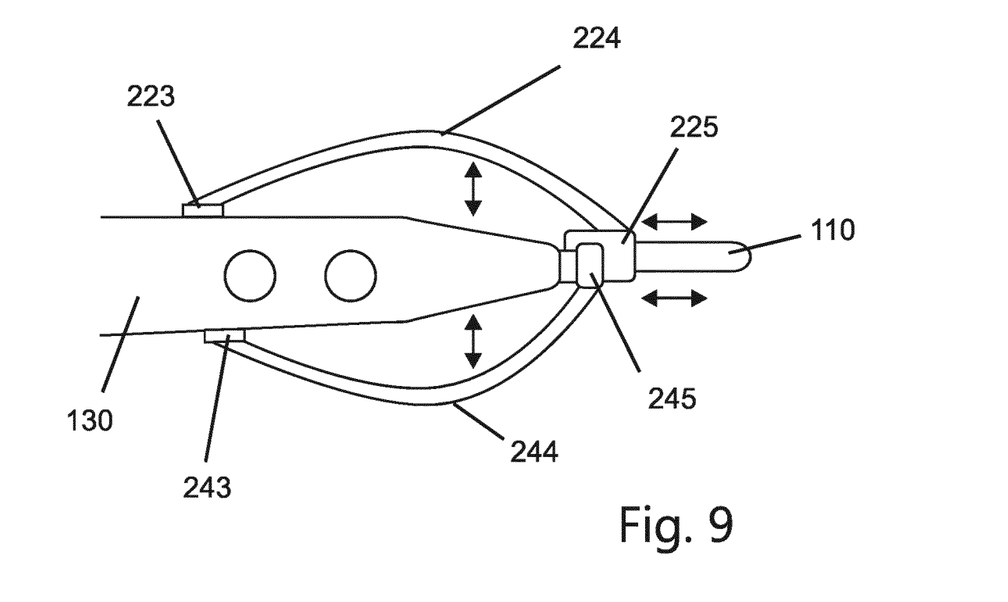
FIG. 9 is a schematic illustration of a further embodiment of a tissue sensing device with an electrosurgical knife.

In another embodiment (FIG. 9), an intermediate portion of at least one of elements 220 and 240 may be made semi rigid which could be contracted as indicated by the double arrows in the figure. This contractile movement could help the distal end 225 and/or 245 to slide over the blade 110 of the knife. This could help the mechanical part to easily move over the knife part. Also this arrangement could enable with easy movement, the help of cleaning the blade more easily.

Figure 10:
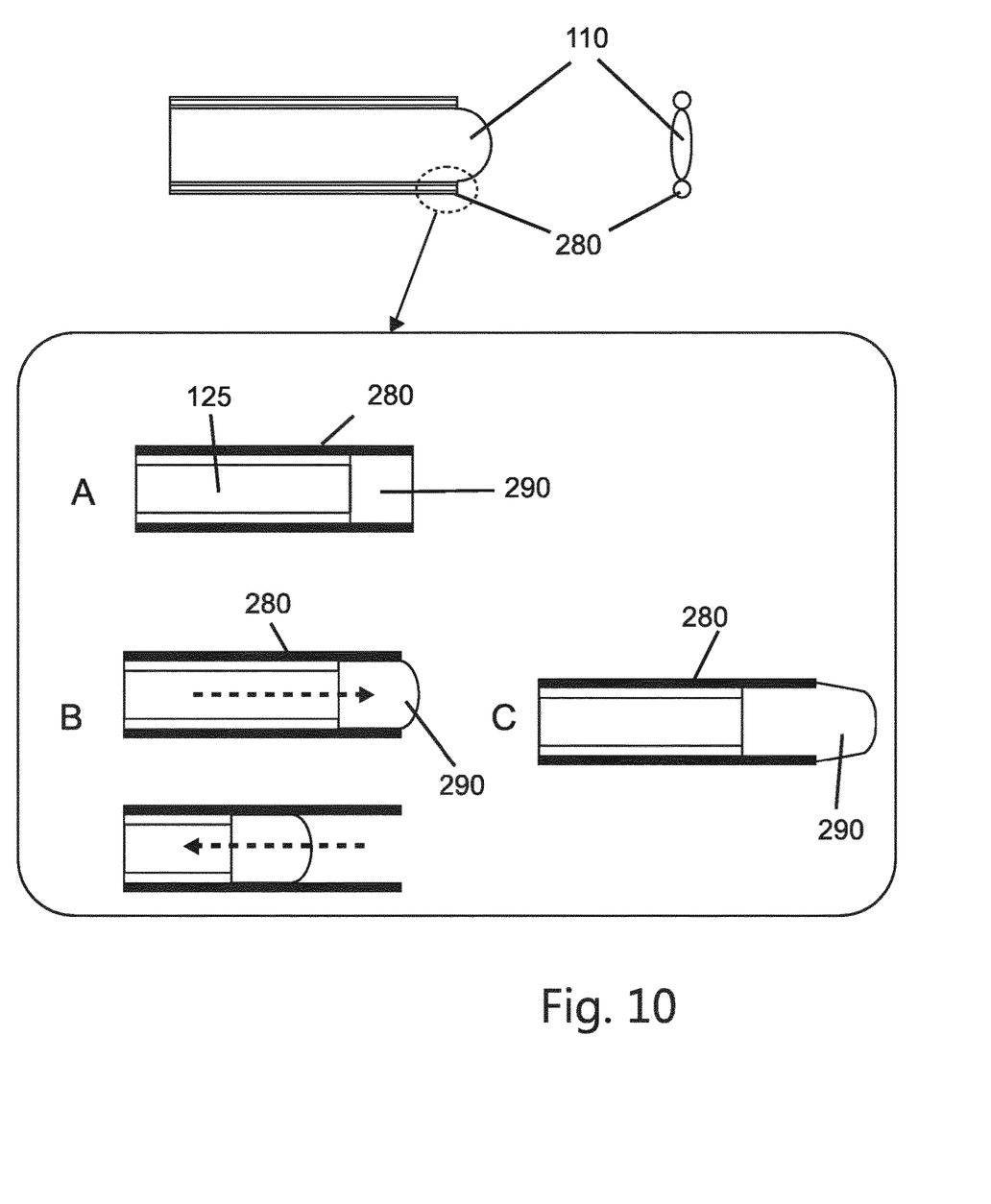
FIG. 10 is an illustration of a distal end portion of a blade together with guiding tubes for optical fibers as well as detail views of the guiding tubes.

In a further embodiment shown in FIG. 10, the optical fibers can be positioned inside guiding tubes 280 mounted to the blade 110 of the surgical knife. The guiding tubes exit next to the distal end of the blade. Inside the tubes 280, moveable optical fibers 120 can be positioned with a small optical plug 290 at the tip consisting of an optically transparent, non-absorbing, heat-resistant material. In the detailed illustrations of FIGS. 10 A, B and C, plugs with different shapes are depicted. The purpose of this plug 290 is to protect the optical fiber ends 125 from getting in direct contact with sparks and/or debris during the cutting process. This is important since the optical fibers consist of multiple, layered components (fiber core/cladding/protective buffer). Moving the fibers repeatedly during use of the device may reduce the optical quality of the fibers, which can be prevented by sealing them with such a protective, optical plug, thus providing optimized light coupling from the tissue into the fibers and vice versa. This can be done by adding isotropically scattering particles to the optical material. This allows for photons entering the plug material from any angle to be collected by the optical fibers. The plug material may consist of a glue/resin which forms a solid finishing of the optical fiber end.

The plug may slightly protrude out of the guiding tubes to reduce the sticking of debris at the plug, and for further optimizing the light coupling towards the fibers. For example, the plug can be designed with a smooth, sphere-like shape, as shown in the detailed view of FIG. 10B. The solutions described above provide additional protection for the retractable fiber ends during operation of the device end for ensuring that the fibers are free of debris when moving them back to the distal end of the tube after cutting.

In addition, the plug may also provide sufficient protection for the fibers to allow for continuous measurements during the entire procedure. In that case, the fibers do not even need to be moveable and could be fixed permanently in their measurement position inside the guiding tubes. For such a fixed, static solution, the optical plug can be designed in a way that the finishing also smooths the edges of the guiding tubes, as shown in detail view of FIG. 10C.

Figure 11:
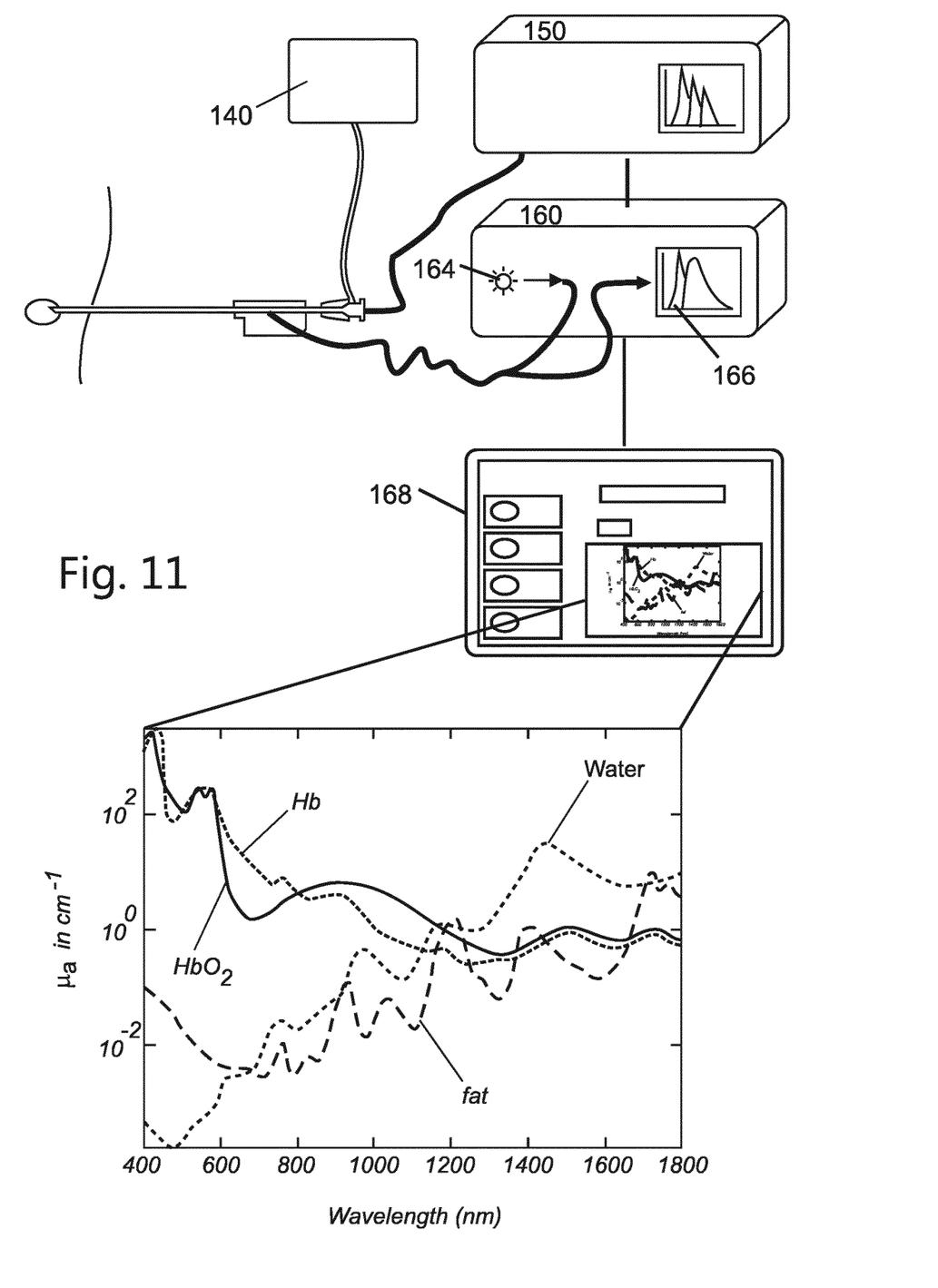
FIG. 11 shows a system according to an embodiment as well as a log plot of the absorption coefficients of blood, water and fat.

As shown in FIG. 11, the optical fibers of the tissue sensing device at the electrosurgical device are connected to an optical console 160. The optical fibers can be understood as light guides or optical waveguides. In an embodiment, the console 160 comprises a light source 164 in the form of a halogen broadband light source with an embedded shutter, and an optical detector 166. The optical detector 166 can resolve light with a wavelength substantially in the visible and infrared regions of the wavelength spectrum, such as from 400 nm to 1700 nm. The combination of light source 164 and detector 166 allows for diffuse reflectance measurements. For a detailed discussion on diffuse reflectance measurements see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

Optionally it is also possible that the console is coupled to an imaging modality capable of imaging the interior of the body, for instance when a resection is taken under image guidance. On the other hand, also other optical methods can be envisioned like diffuse optical tomography by employing a plurality of optical fibers, differential path length spectroscopy, fluorescence and Raman spectroscopy to extract tissue properties.

Further shown in FIG. 11 are an electrosurgical console 150 and a suction device 140. The suction device may be connected to the electrosurgical device, such that underpressure or a vacuum can be applied through the device to the distal end of the same.

A processor transforms the measured spectrum into physiological parameters that are indicative for the tissue state and a monitor 168 may be used to visualize the results.

A computer program executable on the processor may be provided on a suitable medium such as an optical storage medium or a solid-state medium supplied together with or as part of the processor, but may also be distributed in other forms, such as via the Internet or other wired or wireless telecommunication systems.

For fluorescence measurements the optical console must be capable of providing excitation light to at least one source fiber while detecting tissue-generated fluorescence through one or more detection fibers. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fiber as the light for diffuse reflectance. This may be accomplished by, e.g., using a fiber switch, or a beam splitter or dichroic beam combiner with focusing optics. Alternatively, separate fibers may be used for providing fluorescence excitation light and light for diffuse reflectance measurements.

To perform spectroscopy, the acquired spectra may be fitted using a custom made Matlab 7.9.0 (Mathworks, Natick, Mass.) algorithm. In this algorithm, a widely accepted analytical model was implemented, namely the model introduced by the reference T. J. Farrel, M. S. Patterson and B. C. Wilson, "A diffusion theory model of spatially resolved, steady-state diffuse reflectance for the non-invasive determination of tissue optical properties", Med. Phys. 19 (1992) p. 879-888, which is hereby incorporated by reference in entirety. The input arguments for the model of this reference are the absorption coefficient $\mu_a(\lambda)$, the reduced scattering coefficient $\mu'_s(\lambda)$ and the center-to-center distance between the emitting and collecting fibers at the tip of the probe.

In the following part, the model will be explained briefly. The used formulas are mainly based on work of Nachabe et al., and reference is thus made to R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442, which is hereby incorporated by reference in entirety, and furthermore reference is made to R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010), which is also hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter a corresponds to the reduced scattering amplitude at this specific wavelength.

$$\mu_s(\lambda) = a\left(\rho_{MR}\left(\frac{\lambda}{\lambda_0}\right)^{-b} + (1-\rho_{MR})\left(\frac{\lambda}{\lambda_0}\right)^{-4}\right)[\text{cm}^{-1}] \quad \text{(Eq. 1)}$$

In this equation the reduced scattering coefficient is expressed as the sum of Mie and Rayleigh scattering where $\rho_R$ is the Mie-to-total reduced scattering fraction. The reduced scattering slope of the Mie scattering is denoted b and is related to the particle size. For a homogeneous distribution of absorbers, the total light absorption coefficient $\mu_a(\lambda)$ can be computed as products of the extinction coefficients and volume fraction of the absorbers (see FIG. 7)

$$\mu_a^{Total} = f_1\mu_a^1 + f_2\mu_a^2 + f_3\mu_a^3 + \quad \text{(Eq. 2)}$$

Instead of modeling the absorption coefficient $\mu_a(\lambda)$ as the sum of absorption coefficients weighted by the respective concentrations of the four chromophores of interest, it was decided to express the tissue absorption coefficient as $$\mu_a^{Tissue}(\lambda) = C(\lambda)v_{Blood}\mu_a^{Blood}(\lambda) + v_{WL}\mu_a^{WL}(\lambda)[\text{cm}^{-1}] \quad \text{(Eq. 3)}$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL}=[\text{Lipid}]+[\text{H}_2\text{O}]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1-\exp(-2R\mu_a^{Blood}(\lambda))}{2R\mu_a^{Blood}(\lambda)} \quad \text{(Eq. 4)}$$

where R denotes the average vessel radius expressed in cm. The absorption coefficient related to blood is given by $$\mu_a^{Blood}(\lambda) = \alpha_{BL}\mu_a^{HbO_2}(\lambda) + (1-\alpha_{BL})\mu_a^{Hb}(\lambda)[\text{cm}^{-1}] \quad \text{(Eq. 5)}$$

where $\mu_a^{HbO_2}(\lambda)$ and $\mu_a^{Hb}(\lambda)$ represent the basic extinction coefficient spectra of oxygenated hemoglobin $HbO_2$ and deoxygenated hemoglobin Hb, respectively. The oxygenated hemoglobin fraction in the total amount of hemoglobin is noted $\alpha_{BL}=[HbO_2]/([HbO_2]+[Hb])$ and is commonly known as the blood oxygen saturation. The absorption due to the presence of water and lipid in the measured tissue is defined as $$\mu_a^{WL}(\lambda) = \alpha_{WL}\mu_a^{Lipid}(\lambda) + (1-\alpha_{WL})\mu_a^{H_2O}(\lambda)[\text{cm}^{-1}] \quad \text{(Eq. 6)}$$

In this case the concentration of lipid related to the total concentration of lipid and water together can be written as $\alpha_{WF}, =[\text{Lipid}]/([\text{Lipid}]+[\text{H}_2\text{O}])$, where [Lipid] and [H$_2$O] correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf. the reference R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442. For further explanation and validation of this theorem reference is made to the reference R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For example by means of the described algorithm optical tissue properties may be derived such as the scattering coefficient and absorption coefficient of different tissue chromophores: e.g. hemoglobin, oxygenated haemoglobin, water, fat etc. These properties are different between normal healthy tissue and diseased (cancerous) tissue.

The main absorbing constituents in normal tissue dominating the absorption in the visible and near-infrared range are blood (i.e. hemoglobin), water and fat. In the lower part of FIG. 11 the absorption coefficient of these chromophores as a function of the wavelength are presented. Note that blood dominates the absorption in the visible range, while water and fat dominate in the near infrared range.

A way to discriminate differences in spectra is by making use of a principal components analysis. This method allows classification of differences in spectra and thus allows discrimination between tissues. Apart from diffuse reflectance also fluorescence may be measured. Then for instance parameters like collagen, elastin, NADH and FAD could be measured too. Especially, the ratio NADH/FAD, which is called the optical redox parameter, is of interest because it is an indicator for the metabolic state of the tissue, as described in Zhang Q., et al. "Turbidity-free fluorescence spectroscopy of biological tissue", Opt. Lett., 2000 25(19), p. 1451-1453, which is changed in cancer cells and assumed to change upon effective treatment of cancer cells.

It is also possible to detect the response of the body to exogenous fluorophores that can be detected by the tissue sensing device. Furthermore, these could also be linked to measurements of the exogenous fluorophores by imaging modalities like optical mammography based on diffuse optical imaging.

The information regarding the progress and whether the area in contact with the interventional device is still safe to cut can be provided in several ways to the physician. For instance a light indicator can be used that when showing a red light still tumor tissue is detected and with green light no tumor and/or optional with yellow system suspects tumor.

Another way is using a sound signal. Yet another way is showing the probability of a critical structure in contact with the device can be shown as a bar on the display. A light indicator can also be incorporated on the surgical knife itself to prevent the surgeon from having to look at an additional screen. A 2-color system could be used to indicate critical structures near the tissue sensing attachment.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 100 electrosurgical knife
110 blade
120 optical fiber
130 housing
140 suction device
150 electrical console
160 optical console
164 light source
166 light detector
168 monitor
170 trigger/switch
180 connection
190 optical connector
195 lever
200 tissue sensing device
210 optical cable
220, 240 element of tissue sensing device
223, 243 proximal portion
224, 244 grip portion
225, 245 distal portion
230 fiber exit
250 cleaning element
260 elastic element
270 recess
280 guiding tube
290 optical plug

The invention claimed is:

1. A tissue sensing device configured for attachment to an electrosurgical knife for a cutting procedure, the tissue sensing device comprising:
a first body having a first body proximal end portion configured to receive a portion of a housing of the electrosurgical knife, a first body distal end portion configured for movably supporting a blade of the electrosurgical knife, and a grip portion between the first body distal end portion and the first body proximal end portion;
a second body having a second body proximal end portion configured to receive a portion of the housing of the electrosurgical knife, a second body distal end portion configured for movably supporting a blade of the electrosurgical knife, wherein the second body proximal end portion is adjacent to the first body distal end portion; and
an optical fiber having a distal end and a proximal end configured to be connected to an optical console, wherein: the distal end of the optical fiber is further arranged at the first body distal end portion such that when the blade is supported by the first body distal end portion, the distal end of the optical fiber is configured to be positioned separately to the blade, and wherein the second body distal end portion is configured to be moved at least partially independently from the first body distal end portion relative to the blade.

2. The tissue sensing device of claim 1, further comprising a guiding tube, wherein the optical fiber is movably accommodated within the guiding tube.

3. The tissue sensing device of claim 2, further comprising a cleaning element arranged and configured for cleaning a tip of the optical fiber when the optical fiber is moving inside the guiding tube.

4. The tissue sensing device of claim 3, wherein the cleaning element comprises a brush arranged in the guiding tube or at the guiding tube.

5. The tissue sensing device of claim 1, further comprising a protection plug which is arranged at the distal end of the optical fiber and which is configured to protect the optical fiber and transmit light therethrough.

6. The tissue sensing device of claim 1, wherein the optical fiber is configured to be moved relative to the first body distal end portion so that the distal end of the optical fiber protrudes beyond the first body distal end portion.

7. The tissue sensing device of claim 1, further comprising a fiber connector for optically connecting the optical fiber to an optical cable for connected to the optical console.

8. The tissue sensing device of claim 1, further comprising the optical console, wherein the optical console is configured for tissue inspection.

9. The tissue sensing device of claim 1, wherein the distal end of the optical fiber is configured to protrude past an end of the blade.

10. The tissue sensing device of claim 9, wherein the tissue sensing device or the electrosurgical knife further comprises a lever for moving the first body distal end portion between a first position in which the first body distal end portion is located at a tip portion of the blade, and a second position in which the first body distal end portion is located near the housing of the electrosurgical knife.

11. The tissue sensing device of claim 9, further comprising an elastic element for biasing the tissue sensing device in a direction to a tip portion of the blade.

12. The tissue sensing device of claim 9, wherein the grip portion is configured to be elastically deformed to move the first body distal end portion relative to the blade.

13. The tissue sensing device of claim 9, wherein the blade is coated with an anti-sticking layer.

14. The tissue sensing device of claim 9, further comprising an electrical console for providing electrical current to the blade of the electrosurgical knife for the cutting procedure.

15. The tissue sensing device of claim 1, wherein when the blade is supported by the first body distal end portion, the first body distal end portion is configured to be moved toward a tip portion of the blade and into a first position to configure the tissue sensing device for sensing a tissue type of a tissue and is configured to be moved toward the housing of the electrosurgical knife and into a second position to configure the electrosurgical knife for cutting the tissue, wherein the blade is configured to remain stationary when the first body distal end portion is moved between the first position and the second position.

16. An electrosurgical knife for a cutting procedure, the electrosurgical knife comprising:
a blade;
a tissue sensing device comprising:
a first body having a first body proximal end portion configured to receive a portion of a housing of the electrosurgical knife, a first body distal end portion configured for movably supporting the blade, and a grip portion between the first body distal end portion and the first body proximal end portion;

a second body having a second body proximal end portion configured to receive a portion of the housing of the electrosurgical knife, a second body distal end portion configured for movably supporting a blade of the electrosurgical knife, wherein the second body proximal end portion is adjacent to the first body distal end portion; and an optical fiber having a distal end and a proximal end configured to be connected to an optical console, wherein: the distal end of the optical fiber is further arranged at the first body distal end portion such that when the blade is supported by the first body distal end portion, the distal end of the optical fiber is configured to be positioned separately to the blade, and wherein the second body distal end portion is configured to be moved at least partially independently from the first body distal end potion relative to the blade.

17. The electrosurgical knife of claim 16, wherein the tissue sensing device further comprises a guiding tube, wherein the optical fiber is disposed within the guiding tube and configured to move within the guiding tube.

18. The electrosurgical knife of claim 16, wherein the tissue sensing device further comprises a protection plug disposed at the first body distal end and configured to protect the optical fiber and transmit light therethrough.

19. The electrosurgical knife of claim 18, further comprising a cleaning element disposed and configured to clean a tip of the optical fiber when the optical fiber is moving inside a guiding tube.

20. The electrosurgical knife of claim 16, wherein the optical fiber is configured to move relative to the first body distal end portion so that the distal end of the optical fiber protrudes beyond the first body distal end portion.

21. The electrosurgical knife of claim 16, wherein when the blade is supported by the first body distal end portion, the first body distal end portion is configured to be moved toward a tip portion of the blade and into a first position to configure the tissue sensing device for sensing a tissue type of a tissue and is configured to be moved toward the housing of the electrosurgical knife and into a second position to configure the electrosurgical knife for cutting the tissue, wherein the blade is configured to remain stationary when the first body distal end portion is moved between the first position and the second position.

22. A system, comprising:
a tissue sensing device configured for attachment to an electrosurgical knife for a cutting procedure, the tissue sensing device comprising:
a first body having a first body proximal end portion configured to receive a portion of a housing of the electrosurgical knife, a first body distal end portion configured for movably supporting a blade of the electrosurgical knife, and a grip portion between the first body distal end portion and the first body proximal end portion;

a second body having a second body proximal end portion configured to receive a portion of the housing of the electrosurgical knife, a second body distal end portion configured for movably supporting a blade of the electrosurgical knife, wherein the second body proximal end portion is adjacent to the first body distal end portion; and an optical fiber having a distal end a proximal end configured to be connected to an optical console, wherein: the distal end of the optical fiber is further arranged at the first body distal end portion such that when the blade is supported by the first body distal end portion, the distal end of the optical fiber is configured to be positioned separately to the blade, and wherein the second body distal end portion is configured to be moved at least partially independently from the first body distal end portion relative to the blade;

wherein the optical console is configured to receive light for spectral analysis;

a processor; and a non-transitory computer-readable medium that stores instructions, which when executed by the processor, cause the processor to: spectrally analyze the received light; identify a spectral signature; and determine from the spectral signature a tissue type in front of or in direct vicinity of the blade.

23. The system of claim 22, further comprising a white light source configured to transmit white light to a tissue, wherein the processor is configured to determine a presence and concentration of chromophores from the white light diffusively reflected from the tissue.

24. The system of claim 23, wherein the processor is further configured to determine a presence and concentration of water, fat content, or both.

25. The system of claim 22, wherein when the blade is supported by the first body distal end portion, the first body distal end portion is configured to be moved toward a tip portion of the blade and into a first position to configure the tissue sensing device for sensing the tissue type of a tissue and is configured to be moved toward the housing of the electrosurgical knife and into a second position to configure the electrosurgical knife for cutting the tissue, wherein the blade is configured to remain stationary when the first body distal end portion is moved between the first position and the second position.

* * * * *

UNITED STATES PATENT AND TRADEMARK OFFICE
CERTIFICATE OF CORRECTION

PATENT NO. : 11,576,717 B2
APPLICATION NO. : 15/570102
DATED : February 14, 2023
INVENTOR(S) : Bierhoff et al.

It is certified that error appears in the above-identified patent and that said Letters Patent is hereby corrected as shown below:

In the Claims

Claim 1, Column 11, Line 56, "a" should be corrected to read --the--.

Claim 16, Column 13, Line 6, "a" should be corrected to read --the--.

Claim 22, Column 14, Line 9, "a" should be corrected to read --the--.

Signed and Sealed this
Twenty-eighth Day of May, 2024

*Katherine Kelly Vidal*

Katherine Kelly Vidal
*Director of the United States Patent and Trademark Office*